(12) United States Patent
Matsuoka et al.

(10) Patent No.: US 7,980,121 B2
(45) Date of Patent: Jul. 19, 2011

(54) DEGRADATION SIMULATOR FOR GAS SENSOR

(75) Inventors: Mikiyasu Matsuoka, Kariya (JP); Tomoo Kawase, Ama-gun (JP); Eiichi Kurokawa, Okazaki (JP)

(73) Assignee: Denso Corporation, Kariya (JP)

( * ) Notice: Subject to any disclaimer, the term of this patent is extended or adjusted under 35 U.S.C. 154(b) by 532 days.

(21) Appl. No.: 12/203,398

(22) Filed: Sep. 3, 2008

(65) Prior Publication Data

US 2009/0056414 A1 Mar. 5, 2009

(30) Foreign Application Priority Data

Sep. 4, 2007 (JP) ................................. 2007-229487

(51) Int. Cl.
*G01M 15/10* (2006.01)
(52) U.S. Cl. .................................. 73/114.69; 73/118.01
(58) Field of Classification Search ............... 73/114.69, 73/114.71, 114.72, 118.01, 118.02
See application file for complete search history.

(56) References Cited

U.S. PATENT DOCUMENTS

| 5,758,632 | A | 6/1998 | Yamashita et al. | |
|---|---|---|---|---|
| 5,964,208 | A | 10/1999 | Yamashita et al. | |
| 6,032,659 | A | 3/2000 | Yamashita et al. | |
| 7,021,300 | B2 * | 4/2006 | Maki et al. | 123/688 |
| 7,499,789 | B2 * | 3/2009 | Toda et al. | 701/109 |

FOREIGN PATENT DOCUMENTS

| JP | 08-285808 | 11/1996 |
|---|---|---|
| JP | 10-206376 | 8/1998 |
| JP | 2004-308466 | 11/2004 |
| JP | 2004-308474 | 11/2004 |
| JP | 2004-308488 | 11/2004 |
| JP | 2004-308574 | 11/2004 |
| JP | 3869338 | 10/2006 |
| JP | 2008-203152 | 9/2008 |

OTHER PUBLICATIONS

Information Offer Form submitted Jan. 29, 2010, in corresponding JP Application No. 2007-229487, with English translation.
Japanese Office Action dated Oct. 20, 2009, issued in corresponding Japanese Application No. 2007-229487, with English translation.

* cited by examiner

*Primary Examiner* — Eric S McCall
(74) *Attorney, Agent, or Firm* — Nixon & Vanderhye PC

(57) ABSTRACT

The degradation simulator is used for a gas sensor including a sensor element having a solid electrolyte layer and a pair of electrodes located opposite to each other across from the solid electrolyte layer, the sensor element outputting a sensor output signal having a value depending on concentration of a specific gas in the ambient gas. The degradation simulator includes a first setting function of enabling variably setting a time constant delay which appears on the sensor output signal when concentration of the specific gas changes, a second setting function of enabling variably setting a dead time delay which appears on the sensor output signal when concentration of the specific gas changes, and an adding function of adding at least one of the time constant delay and dead time delay to the sensor output signal in order to generate a pseudo-degraded sensor output signal in accordance with an external instruction.

14 Claims, 10 Drawing Sheets

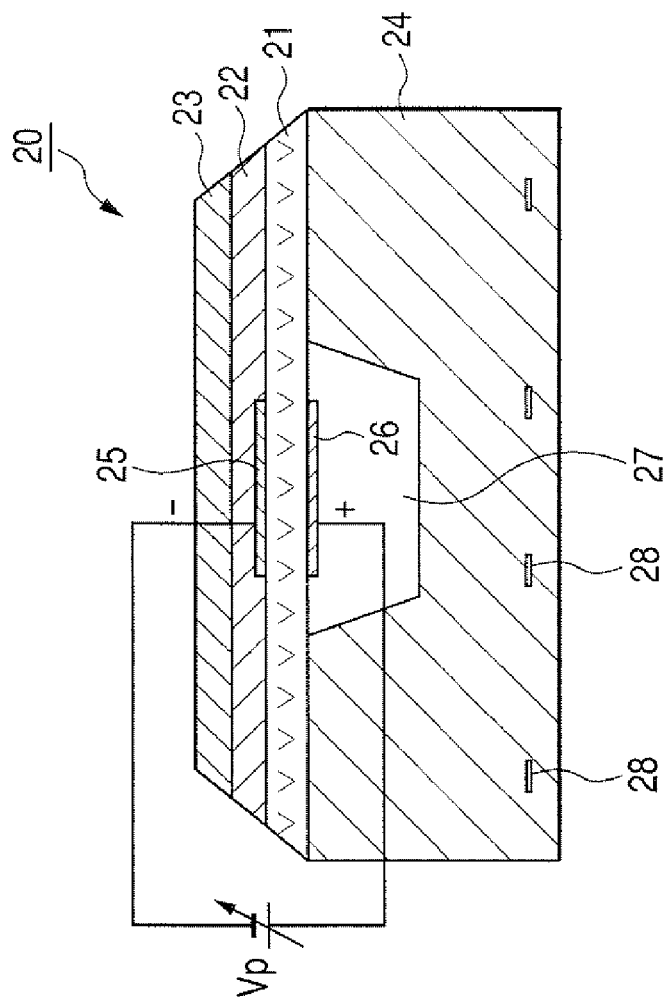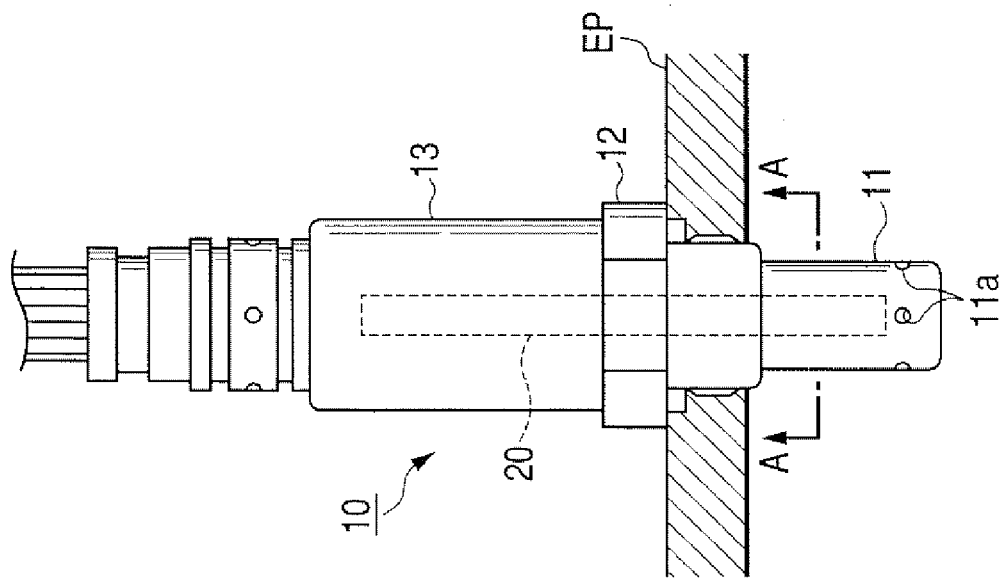

DEGRADATION SIMULATOR FOR GAS SENSOR

CROSS-REFERENCE TO RELATED APPLICATION

This application is related to Japanese Patent Application No. 2007-229487 filed on Sep. 4, 2007, the contents of which are hereby incorporated by reference.

BACKGROUND OF THE INVENTION

1. Field of the Invention

The present invention relates to a degradation simulator for gas sensors.

2. Description of Related Art

There is known a degradation simulator for an oxygen sensor used for measuring oxygen concentration in an exhaust gas of an internal combustion engine, the degradation simulator having a function of setting an output of the oxygen sensor in a pseudo-degraded state for simulation purpose. According to this degradation simulator, it becomes possible to obtain an oxygen sensor (dummy sensor) in a degraded state without performing a lengthy durability test, or taking the trouble to fabricate an oxygen sensor in a degraded state.

As such a degradation simulator, Japanese Patent No. 3869338 discloses an apparatus including a signal processor and a dummy sensor, the signal processor having a function of varying, in accordance with a target degradation, an oxygen pumping current for an oxygen sensor including an oxygen concentration cell and an oxygen pumping cell (the so-called 2-cell sensor), the dummy sensor having a function of varying, in accordance with the target degradation, an element resistance signal and an output signal of the signal processor. This patent document further discloses that the signal processor includes at least one of an offset correction means for varying an offset of the oxygen pumping current, a gain correction means for varying a gain, and a response characteristic correction means for varying a delay of output change (time constant).

Meanwhile, the inventors of the present invention have found that there are various causes that degrade an output of a gas sensor other than degradation of a sensor element of the gas sensor itself. For example, when the gas sensor is exposed to an exhaust gas, adhesion of various substances to an element cover of the gas sensor degrades the output of a gas sensor. Accordingly, since the degradation states which conventional degradation simulators can simulate are limited, the conventional degradation simulators are insufficient in performance for simulating various degradation states that can actually occur in gas sensors.

SUMMARY OF THE INVENTION

The present invention provides a degradation simulator for a gas sensor including a sensor element having a solid electrolyte layer and a pair of electrodes located opposite to each other across from the solid electrolyte layer, and an element cover surrounding the sensor element and formed with a vent hole to introduce an ambient gas into the sensor element, the sensor element outputting a sensor output signal having a value depending on concentration of a specific gas in the ambient gas, the degradation simulator comprising:

a first setting function of enabling variably setting a time constant delay which appears on the sensor output signal when concentration of the specific gas changes;

a second setting function of enabling variably setting a dead time delay which appears on the sensor output signal when concentration of the specific gas changes; and an adding function of adding at least one of the time constant delay set by the first function and the dead time delay set by the second function to the sensor output signal in order to generate a pseudo-degraded sensor output signal in accordance with an external instruction.

According to the present invention, it is possible to provide a degradation simulator for a gas sensor, which enables simulating various kinds of degradations, and accordingly is excellent in practicality.

Other advantages and features of the invention will become apparent from the following description including the drawings and claims.

BRIEF DESCRIPTION OF THE DRAWINGS

In the accompanying drawings:

FIG. 3A is an external view of and A/F sensor as a simulation object of the degradation simulator;

FIG. 3B is a cross-sectional view of the A/F sensor;

PREFERRED EMBODIMENTS OF THE INVENTION

First Embodiment

Figure 1:
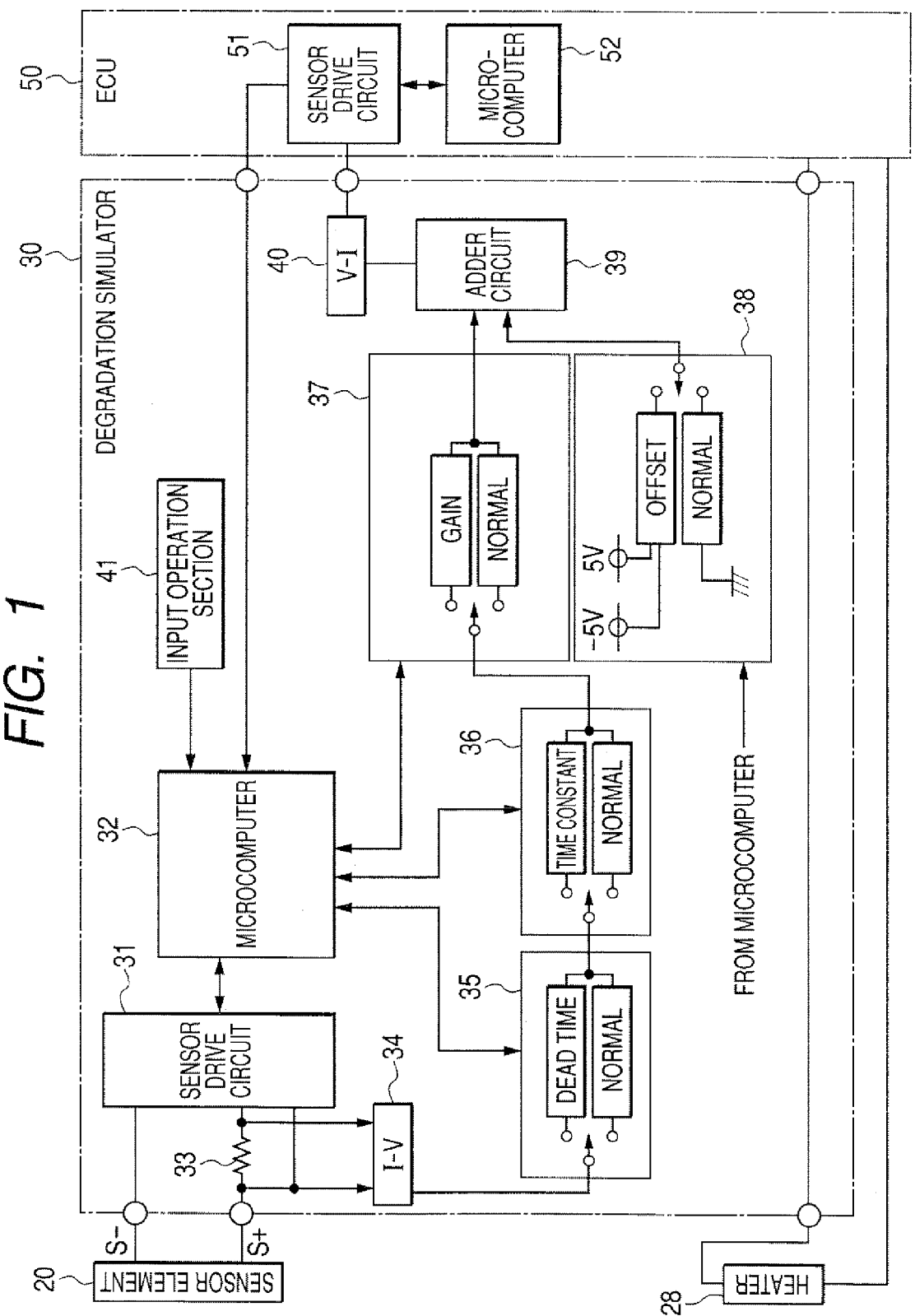
FIG. 1 is a diagram showing a structure of a degradation simulator for an A/F sensor (air-fuel ratio sensor) according to a first embodiment of the invention.

The degradation simulator according to a first embodiment of the invention is for performing a degradation simulation on an A/F sensor (air-fuel ratio sensor) used for measuring an oxygen concentration in an exhaust gas (combustion gas) discharged from a vehicle-mounted gasoline engine.

First, the structure of the A/F sensor is explained with reference to FIGS. 3A and 3B. FIG. 3A is an external view of the A/F sensor 10. FIG. 3B is a cross-sectional view of a sensor element 20 included in the A/F sensor 10 (a cross section of FIG. 3A take along A-A excluding a front side cover 11 of the A/F sensor 10).

As shown in FIG. 3A, the A/F sensor 10, which has roughly a cylindrical shape on the whole, includes the front side cover 11, a housing 12, and a rear side cover 13. In the A/F sensor 10, the sensor element 20 having a slender shape is disposed. The A/F sensor 10 is configured to be mountable to a wall of an exhaust pipe EP at the housing 12. When the A/F sensor 10 is mounted to the wall EP, the front side cover 11 is located inside the exhaust pipe EP, so that the exhaust gas is supplied to the sensor element 20 through a plurality of small vent holes formed in the front side cover 11. The sensor element 20 has a laminated structure. Although not shown in the drawing, the front side cover 11 has a double structure including an inner cover and an outer cover. The inner and outer covers are formed with a plurality of small holes 11a so as not to overlap one another to prevent water entry.

As shown in FIG. 3B, the sensor element 20 includes a solid electrolyte layer 21, a diffusion resistance layer 22, a shield layer 23, and an insulating layer 24, which are laminated successively. The sensor element 20 is provided with a not shown protection layer at its circumference. The solid electrolyte layer 21, which has a rectangular plate shape, is made of a sheet of partially stabilized zirconia. A pair of electrodes 25 and 26 are located opposite to each other across from the solid electrolyte layer 21. The electrodes 25, 26 are made of noble metal such as platinum Pt. The diffusion resistance layer 22, which is for introducing the exhaust gas into the electrode 25, is made of a porous sheet. The shield layer 23 is a dense layer impermeable to the exhaust gas. The diffusion resistance layer 22 and the shield layer 23 are both made by forming ceramic such as alumina or zirconia in a shape of sheet. However, they have different gas permeabilities due to difference in their average porosity diameters and porosity ratios.

The insulating layer 24, which is made of ceramic such as alumina or zirconia, is formed with an atmosphere duct 27 at a portion facing the electrode 26. The insulating layer 24 includes a heater 28 of a filament shape made of Pt embedded therein. The heater 28 generates heat when supplied with electric power from a battery source to heat the whole of the sensor element 20. The heater 28 may be located external of the sensor element 20 instead of being embedded in the sensor element 20.

When a predetermined voltage is applied across the electrodes 25 and 26, a current depending on oxygen concentration in the exhaust gas flows as an element current through the solid electrolyte layer 21. On the basis of measurement of the element current, the oxygen concentration (A/F) is calculated.

Next, the degradation simulator 30 of this embodiment which performs a degradation simulation on the above described A/F sensor 10 is explained with reference to FIG. 1.

As shown in FIG. 1, the degradation simulator 30 is connected with the sensor element 20 and the heater 28 of the A/F sensor 10, and also an ECU (Electronic Control Unit) 50.

The ECU 50 is an engine ECU which controls a fuel injection amount from each fuel injection valve, and injection timing of an ignition device in accordance with a running state of the engine at every moment of time. To detect an air-fuel ratio, the ECU 50 includes a sensor drive circuit 51 to drive the A/F sensor 10, and a microcomputer 52 including a CPU and various memories. When the engine is in a normal running state, an A/F measurement signal (a sensor output) outputted from the A/F sensor 10 is inputted into the sensor drive circuit 51 in succession. The A/F measurement signal is amplified in the sensor drive circuit 51, and then inputted into the microcomputer 52. The sensor drive circuit 51 is provided with, in addition to the signal amplifying function, an application voltage control function of variably setting the sensor application voltage (the voltage applied to the A/F sensor 10) in accordance with the sensor output, and an impedance measuring function of measuring a resistance (an element impedance) of the sensor element 20.

As explained above, when the engine is in a normal running state, the A/F sensor 10 is directly connected to the ECU 50 so that the A/F sensor 10 is driven by the sensor drive circuit 51 of the ECU 50. In this state, the process for amplifying the A/F measurement signal, the process for variably setting the sensor application voltage, and the process for measuring the element impedance are performed by the sensor drive circuit 51.

The degradation simulator 30 also includes a sensor drive circuit 31 and a microcomputer 32. The sensor drive circuit 31 is connected with a negative terminal S− of the sensor element 20, and connected with a positive terminal S+ of the sensor element 20 through a current measuring resistor 33 provided to measure the element current flowing through the sensor element 20. Basically, the sensor drive circuit 31 and the microcomputer 32 are respectively the same in structure as the sensor drive circuit 51 and the microcomputer 52 of the ECU 50. That is, the sensor drive circuit 31 is provided with a signal amplifying function, a application voltage control function, and an impedance measuring function. Although not shown in the drawing, like the degradation simulator 30, the ECU 50 also includes a current measuring resistor.

The degradation simulator 30 is further provided with a pseudo-degradation setting function to set the sensor output in a pseudo-degraded state in which the element current (the sensor output) measured by the current measuring resistor 33 is added with a pseudo-degradation component. In the following, details of the pseudo-degradation setting function are explained.

First, pseudo-degradation mode is explained. In this embodiment, the pseudo-degradation mode includes the following modes.
(a) A dead time variable mode
(b) A time constant variable mode
(c) A gain variable mode
(d) An offset variable mode In at least one of the above modes (a) to (d), the state of a pseudo-degradation is variably set. In this embodiment, it is possible to control switching between ON/OFF, and to turn on two or more of the modes (a) to (d) at the same time. Of the modes (a) to (d), the mode (a) and the mode (b) are modes concerning response degradation.

In each of the dead time variable mode and the time constant variable mode, it is possible to control a pseudo-degraded state individually for each of a lean side shift at which the air-fuel ratio is shifted to a rich side to a lean side, and a rich side shift at which the air-fuel ratio is shifted to a lean side to a rich side. This makes it possible to generate a pseudo-degradation state in either a symmetrical mode or an asymmetrical mode.

In each of the above modes (a) to (d), a volume adjustment is possible. That is, in this embodiment, it is possible to perform a dead time volume adjustment in the dead time variable mode, a time constant volume adjustment in the time constant variable mode, a gain volume adjustment in the gain variable mode, and an offset volume adjustment in the offset variable mode.

To this end, as shown in FIG. 1, the degradation simulator 30 is provided with a dead time setting circuit 35, a time constant setting circuit 36, a gain setting circuit 37, and an offset setting circuit 38. The dead time setting circuit 35, the time constant setting circuit 36, and the gain setting circuit 37 are connected in series. An output of the gain setting circuit 37 and an output of the offset setting circuit 38 are inputted to an adder circuit 39. In the offset setting circuit 38, an offset voltage is set within a range of from a predetermined negative voltage (−5 V) to a predetermined positive voltage (+5 V) when offset is needed. The offset voltage is set to 0 V when offset is not needed.

Each of the dead time setting circuit 35, time constant setting circuit 36, gain setting circuit 37, and offset setting circuit 38 is switchable between a degradation simulating state in which a pseudo-degradation component is added to the sensor output, and a normal state in which any pseudo-degradation component is not added to the sensor output. Switching between the degradation simulating state and the normal state is performed in accordance with a command signal from the microcomputer 32. From the microcomputer 32 to each of the circuits 35 to 38, a command signal and a volume signal are inputted as necessary, the command signal designating in which of the lean side shift and the rich side shift the pseudo-degradation state should be set, the volume signal designating the value of the volume adjustment in each of the above variable modes. In this embodiment, a dead time, which appears on the sensor output when the air-fuel ratio changes, is set by the dead time setting circuit 35, and a time constant delay, which appears on the sensor output when the air-fuel ratio changes, is set by the time constant setting circuit 36 in accordance with directions (software process) from the microcomputer 32.

In the degradation simulator 30 having the above described structure, the element current measured by the current measuring resistor 33 is inputted to the dead time setting circuit 35 through an I-V converter 34, and thereafter, inputted to the adder circuit 39 through the time constant setting circuit 36 and the gain setting circuit 37. In more detail, the adder circuit 39 is inputted with a voltage signal corresponding to the element current added with a degradation component associated with at least one of the dead time (the dead time delay), the time constant (time constant delay), and the gain, and also inputted with a voltage signal corresponding to the element current not added with the degradation component, that is, a voltage signal corresponding to the original sensor output (element current). In the adder circuit 39, the voltage signal inputted through the setting circuits 35 to 37 is added with the output (the offset setting voltage) of the offset setting circuit 38, and then outputted to the sensor drive circuit 51 of the ECU 50 through a V-I converter circuit 40.

The degradation simulator 30 is provided with an input operation section 41 enabling a user to perform input operations including setting of the pseudo-degradation mode, switching between the symmetrical/asymmetrical modes, and the volume adjustment. The results of operation performed to the input operation section 41 are taken in by the microcomputer 32. The input operation section 41 may be integrally mounted to a case of the degradation simulator 30. Alternatively, the input operation section 41 may be a keyboard input device.

Figure 2:
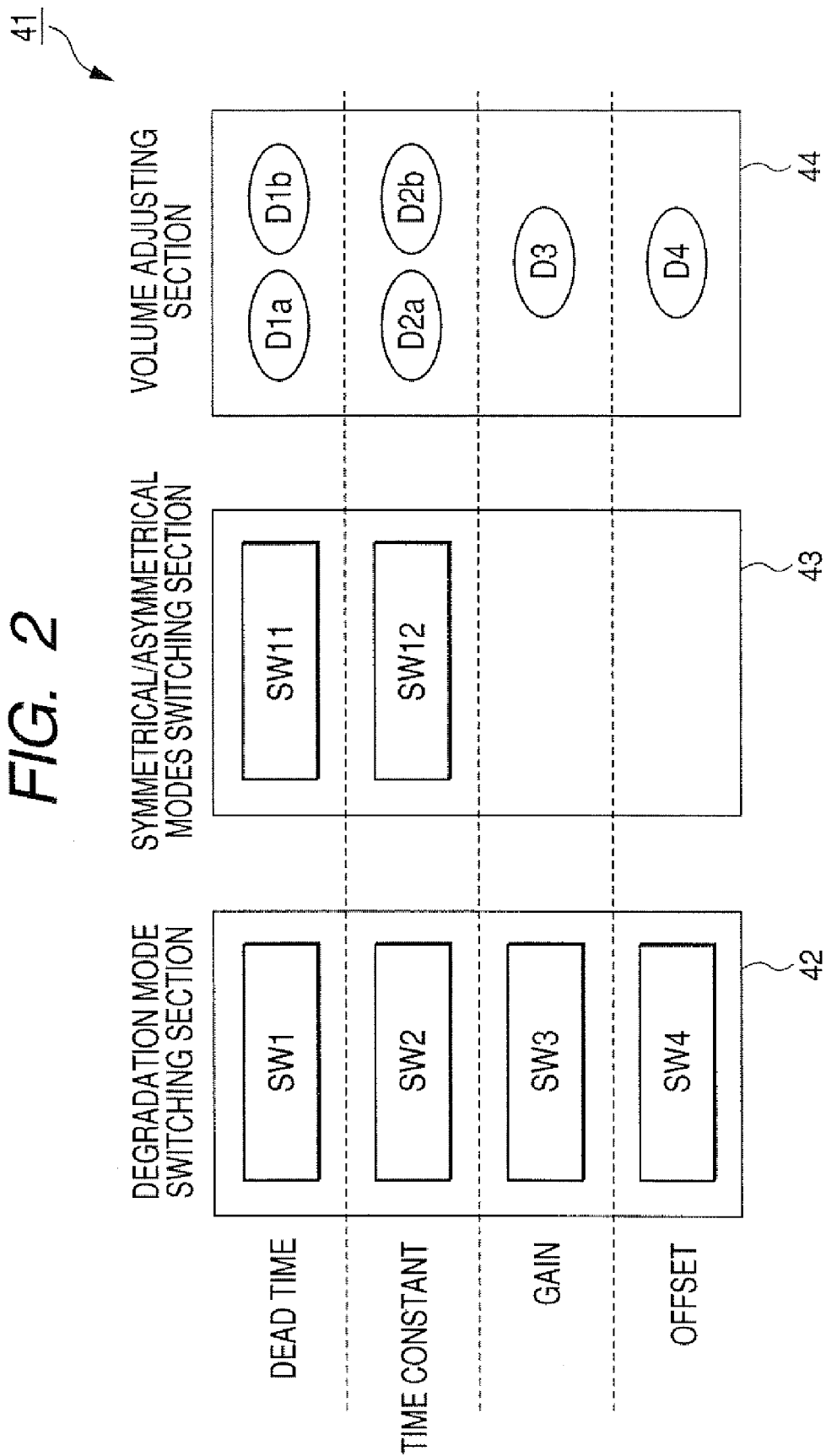
FIG. 2 is a diagram showing a structure of an input operation section included in the gradation simulator shown in FIG. 1.

As shown in FIG. 2, the input operation section 41 includes a degradation mode switching section 42, a symmetrical/asymmetrical modes switching section 43, and a volume adjusting section 44. The degradation mode switching section 42 includes a changeover switch SW1 to select between the dead time variable mode and the normal mode for dead time pseudo-degradation, a changeover switch SW2 to select between the time constant variable mode and the normal mode for time constant pseudo-degradation, a changeover switch SW3 to select between the gain variable mode and the normal mode for the gain pseudo-degradation, and a changeover switch SW4 to select between the offset variable mode and the normal mode for offset pseudo-degradation.

The symmetrical/asymmetrical modes switching section 43 includes a changeover switch SW11 to select a symmetrical mode or an asymmetrical mode for a degradation extent at the lean side shift and a degradation extent at the rich side shift in generating a dead time pseudo-degradation, and includes a changeover switch SW12 to select a symmetrical mode or an asymmetrical mode for a degradation extent at the lean side shift and a degradation extent at the rich side shift in generating the time constant pseudo-degradation.

The volume adjusting section 44 includes adjustment dials D1, D2, D3 and D4 to perform volume adjustment in generating the dead time pseudo-degradation, time constant pseudo-degradation, gain pseudo-degradation, and offset pseudo-degradation, respectively. In this embodiment, since the lean side shift and the rich side shift can be made asymmetrical for the dead time pseudo-degradation and the time constant pseudo-degradation, adjustment dials D1a and D2a to adjust the lean side shift are provided, and adjustment dials D1b and D2b to adjust the lean side shift are provided respectively for the dead time pseudo-degradation and the time constant pseudo-degradation. In this embodiment, when adjustment volumes are symmetrical between the lean side shift and the rich side shift, the time constant and the dead time can be adjusted by operating only one of each two adjustment dials (D1a or D2a, for example), which serves as a double-purpose lean/rich adjustment dial.

Figure 4:
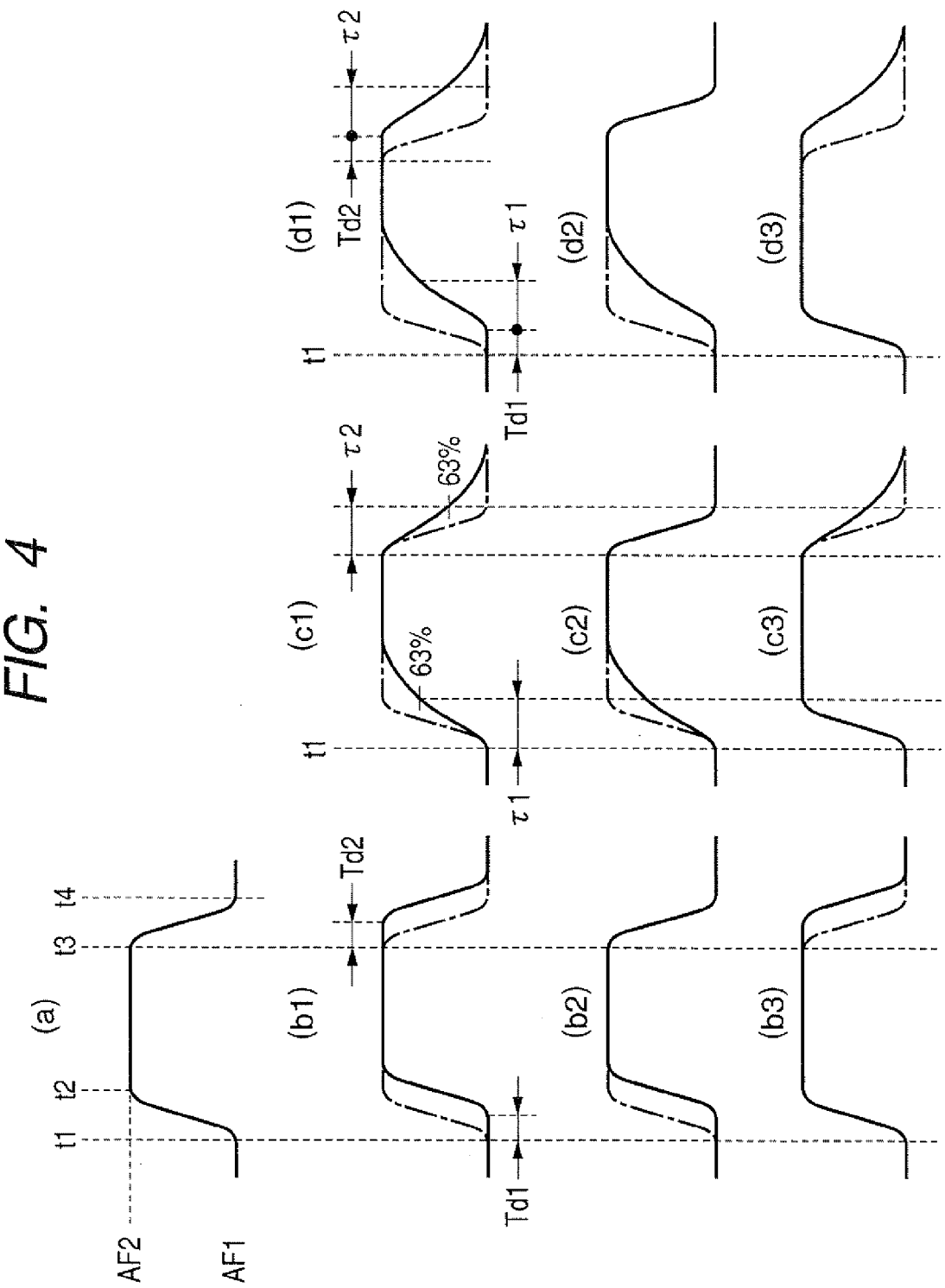
FIG. 4 is a time chart showing transition over time of a sensor output of the A/F sensor at the time of performing degradation simulation.

Next, transition over time of the sensor output (the A/F measurement signal outputted from the degradation simulator 30 to the ECU 50) at the time of executing a degradation simulation is explained with reference to the time chart of FIG. 4. In FIG. 4, the bracket (a) shows a normal (reference) waveform (or transition slope), and each of the brackets (b1) to (b3), (c1) to (c3), and (d1) to (d3) shows a pseudo-degraded waveform. In all of the brackets except the bracket (a), the normal waveform is shown by a chain line. The transitions of the A/F measurement signal shown in FIG. 4 are caused by changing the environmental atmosphere of the sensor element 20, that is, the gas atmosphere in the exhaust pipe between rich and lean.

In the case shown in the bracket (a), the value of the A/F measurement signal (may be referred to simply as the "A/F" hereinafter) starts changing from AF1 (a predetermined rich side value) at timing t1, and converges to AF2 (a predetermined lean side value) at timing t2. Thereafter, the A/F starts changing from AF2 at timing t3, and converges to AF1 at timing t4. The timing t1 is a start timing of the change to the lean side, and the timing t3 is a start timing of the change to the rich side.

On the other hand, in the cases of the brackets (b1) to (b3), which simulate the dead time degradation, a value Td1 is set as the dead time at the time of the lean side shift, and a value Td2 is set as the dead time at the time of the rich side shift. More specifically, in the case of the bracket (b1), the dead time variable mode is turned on in both of the lean side shift and the rich side shift (that is, in FIG. 2, the changeover switch SW1 selects the dead time variable mode, and the changeover switch SW11 selects the symmetrical mode), and the values Td1 and Td2 are set as the dead times for the lean side shift and the rich side shift, respectively. At this time, by operating the adjustment dial D1a serving as a double-purpose lean/rich adjustment dial, the dead times Td1 and Td2 can be variably set (Td1=Td2).

In contrast, in the cases of the brackets (b2) and (b3), the dead time variable mode is turned on only one of the lean side shift and the rich side shift. That is, in the cases of the brackets (b2) and (b3), the changeover switch SW1 selects the dead time variable mode, and the changeover switch SW11 selects the asymmetrical mode. In the case of the bracket (b2), only the adjustment dial D1a for the lean side shift is adjusted to variably set the dead time Td1. In the case of the bracket (b3), only the adjustment dial D1b for the rich side shift is adjusted to variably set the dead time Td2.

In the cases of the brackets (c1) to (c3), which simulate the constant time degradation, a value $\tau 1$ is set as the constant time at the time of lean side shift, and a value $\tau 2$ is set as the constant time at the time of the rich side shift. In more detail, in the case of the bracket (c1), the constant time variable mode is turned on in both of the lean side shift and the rich side shift (that is, in FIG. 2, the changeover switch SW1 selects the constant time variable mode, and the changeover switch SW12 selects the symmetrical mode), and the values $\tau 1$ and $\tau 2$ are set as the constant times for the lean side shift and the rich side shift, respectively. At this time, by operating the adjustment dial D2a serving as a double-purpose lean/rich adjustment dial, the constant times $\tau 1$ and $\tau 2$ can be variably set ($\tau 1 = \tau 2$). In this embodiment, the time constant is the time needed for the sensor output to reach 63% of its final value.

Contrarily, in the cases of the brackets (c2) and (c3), the constant time variable mode is turned on only one of the lean side shift and the rich side shift. That is, in the cases of the brackets (c2) and (c3), the changeover switch SW2 selects the constant time variable mode, and the changeover switch SW12 selects the asymmetrical mode. In the case of the bracket (c2), only the adjustment dial D2a for the lean side shift is adjusted to variably set the constant time z1. In the case of the bracket (c3), only the adjustment dial D2b for the rich side shift is adjusted to variably set the constant time $\tau 2$.

In the cases of the brackets (b1) to (b3), which simulate both the dead time degradation and constant time degradation, the value Td1 and the value $\tau 1$ are respectively set as the dead time and time constant at the time of the lean side shift, and the value Td2 and the value $\tau 2$ are respectively set as the dead time and time constant at the time of the rich side shift. In more detail, in the case of the bracket (d1), the dead time variable mode and the time constant variable mode are turned on in both of the lean side shift and the rich side shift, (that is, in FIG. 2, the changeover switch SW1 selects the dead time variable mode, the changeover switch SW2 selects the constant time variable mode, and the changeover switches SW11 and SW2 select the symmetrical mode), the values Td1 and Td2 are set as the dead times for the lean side shift and the rich side shift, respectively, and the values $\tau 1$ and $\tau 2$ are set as the constant times for the lean side shift and the rich side shift, respectively. At this time, by operating the adjustment dials D1a and D2a each serving as a double-purpose lean/rich adjustment dial, the dead times Td1 and Td2, and the constant times $\tau 1$ and $\tau 2$ can be variably set (Td1=Td2, $\tau 1 = \tau 2$).

Contrarily, in the cases of the brackets (d2) and (d3), the constant time variable mode and the time constant variable mode are turned on only one of the lean side shift and the rich side shift. That is, in the cases of the brackets (d2) and (d3), the changeover switch SW1 selects the dead time variable mode, the changeover switch SW2 selects the constant time variable mode, and the changeover switches SW11 and SW12 each select the asymmetrical mode. In the case of the bracket (d2), the adjustment dials D1a and D2a for the lean side shift are adjusted to variably set the dead time Td1 and constant time $\tau 1$. In the case of the bracket (d3), the adjustment dials D1b and D2b for the rich side shift are adjusted to variably set the dead time Td2 and constant time $\tau 2$.

Figure 5A:
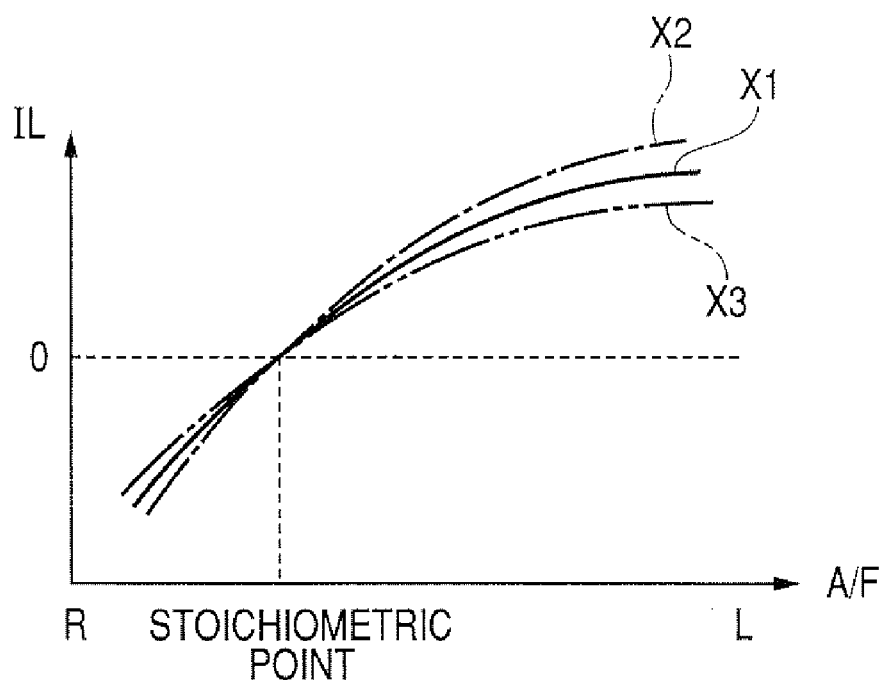
FIG. 5A is a graph showing a relationship between IL (element current) of the A/F sensor and A/F (air-fuel ratio) when gain degradation is present.
Figure 5B:
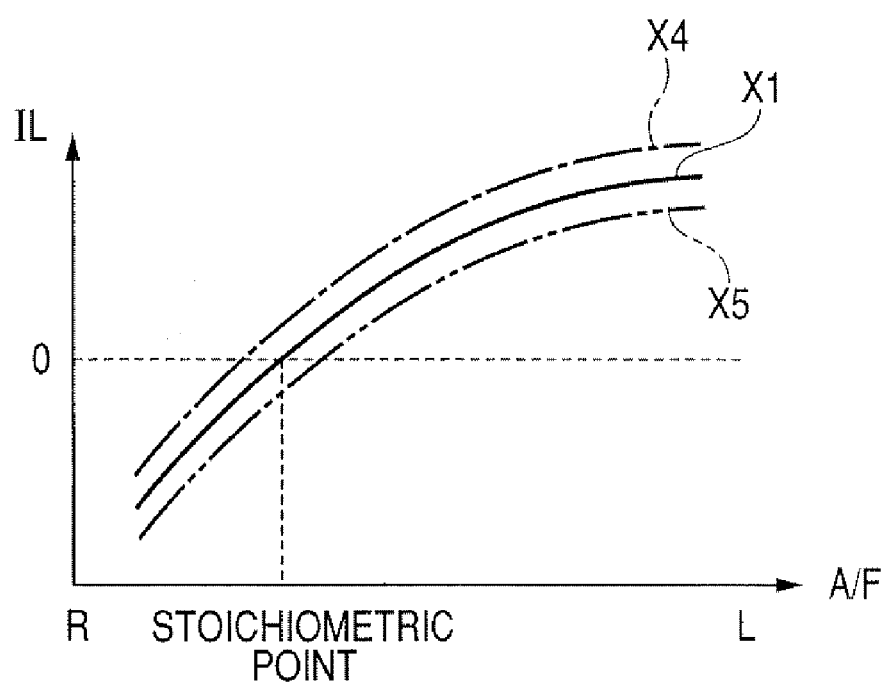
FIG. 5B is a graph showing a relationship between IL (element current) of the A/F sensor and A/F (air-fuel ratio) when offset degradation is present.

The degradation simulator 30 of this embodiment can perform, in addition to the above described degradation simulation concerning response degradation, degradation simulations concerning gain degradation and offset degradation as explained below. Each of FIG. 5A and FIG. 5B is a graph showing a relationship between A/F (an air-fuel ratio) and the element current IL as the sensor characteristic of the A/F sensor. FIG. 5A shows a case when gain degradation is present, and FIG. 5B shows a case when offset degradation is present. In FIG. 5A, the solid line represents a basic sensor characteristic X1 including no degradation, and the chain line X2 and chain double-dashed line X3 respectively represent gain-degraded sensor characteristics X2 and X3. In FIG. 5B, the solid line represents the basic sensor characteristic X1 including no degradation, and the chain line X4 and chain double-dashed line X5 respectively represent offset-degraded sensor characteristics X4 and X5.

When a degradation simulation concerning gain degradation is performed, the changeover switch SW3 is operated to select the gain variable mode, and a gain G is variably set by operating the gain volume adjustment dial D3. By these operations, the gain-degraded sensor characteristics X2 and X3, each of which is equivalent to the basic sensor characteristic X1 added with a gain degradation component, can be realized.

When a degradation simulation concerning offset degradation is performed, the changeover switch SW4 is operated to select the offset variable mode, and an offset F is variably set by operating the offset volume adjustment dial D4. By these operations, the offset-degraded sensor characteristics X4 and X5, each of which is equivalent to the basic sensor characteristic X1 added with an offset degradation component, can be realized.

The gain setting and offset setting as described above may be performed at the time of performing the degradation simulation concerning dead time degradation or constant time degradation which have been explained with reference to FIG. 4. Alternatively, the gain setting and the offset setting may be performed independently of the degradation simulation concerning dead time degradation or constant time degradation, that is, they may be performed without setting the dead time or time constant.

The first embodiment described above provides the following advantages.

By the provision of the time constant variable mode as the pseudo-degradation mode, it is possible to suitably simulate degradation caused by contamination of the element electrode (the electrode 25 in FIG. 3) exposed to the exhaust gas atmosphere, or clogging of the porous diffusion resistance layer (the diffusion resistance layer 22). By the provision of the dead time variable mode as the pseudo-degradation mode, it is possible to suitably simulate degradation caused by clogging of the small holes 11a of the front side cover 11. By the configuration in which the time constant variable mode and the dead time variable mode can be set at the same time, it is possible to suitably simulate degradation caused when the contamination of the element electrode, and the clogging of the small holes 11a of the porous diffusion resistance layer or the front side cover 11 occur at the same time. This embodiment enables simulating various kinds of degradations, and accordingly is excellent in practicality.

By the configuration in which volume adjustment can be performed either symmetrically or asymmetrically between the lean side shift and the rich side shift, it is possible to simulate degradation whose extent differs between the lean side shift and the rich side shift. For example, the contamination degree of the sensor element differs between the electrode at the exhaust gas side and the electrode at the atmosphere side, because the electrode at the exhaust gas side is contaminated earlier. In more detail, since the exhaust gas side electrode is contaminated by Pb etc., the response characteristic of the sensor is lowered for a rich gas. According to this embodiment, it is possible to suitably perform a degradation simulation for such a case by taking into account the difference in the response characteristic between the lean side shift and rich side shift.

In this embodiment, since the time constant and the dead time can be adjusted by the adjustment dials provided respectively for the lean side shift and the rich side shift, when adjustment volumes are asymmetrical between the lean side shift and the rich side shift, they can be set to their respective desired values. Also, when adjustment volumes are symmetrical between the lean side shift and the rich side shift, the time constant and the dead time can be adjusted by operating only one of each two adjustment dials (D1a or D2a, for example), which serves as a double-purpose lean/rich adjustment dial. This improves the operability for performing simulation.

Furthermore, since the gain variable mode and the offset variable mode are additionally provided, a variety of the degradation simulation can be further improved.

Second Embodiment

Figure 6:
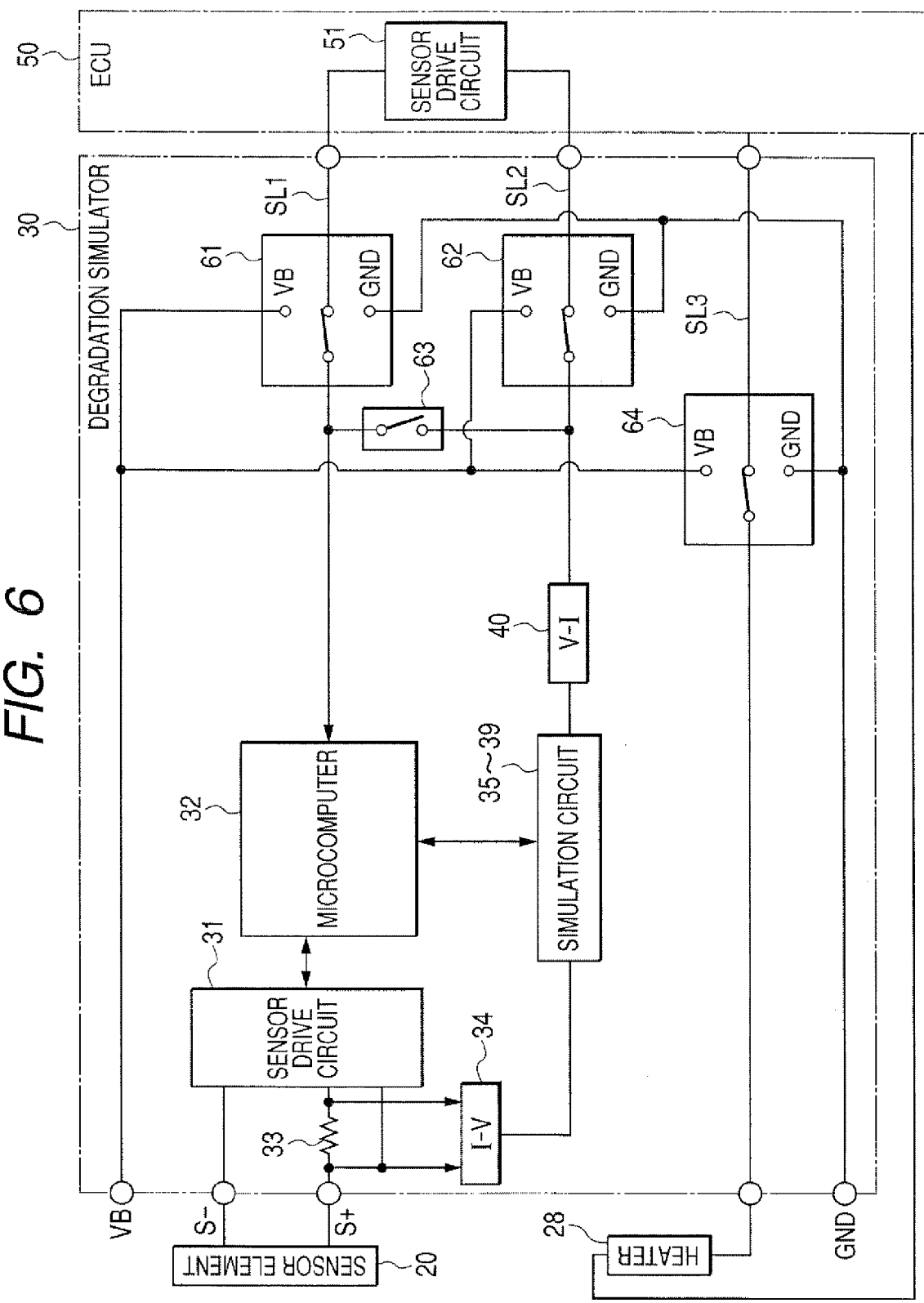
FIG. 6 is a diagram showing a structure of a degradation simulator for an A/F sensor (air-fuel ratio sensor) according to a second embodiment of the invention.

The degradation simulator of a second embodiment of the invention has a structure to enable performing, in addition to the degradation simulations concerning response delay (dead time delay, and time constant delay), abnormality simulations concerning abnormalities such as disconnection or short circuit in an electrical line leading to the sensor element 20 or heater 28. FIG. 6 is a diagram showing the structure of the degradation simulator 30 of the second embodiment. In FIG. 6, the same reference numerals or characters as those in FIG. 1 respectively indicate the same or corresponding components or portions. In FIG. 6, the "simulation circuit" is equivalent to the circuits 35 to 38 shown in FIG. 1.

The degradation simulator 30 includes a switch circuit 61 which outputs the negative terminal voltage of the sensor element 20 to the ECU 50 through a signal line SL1 when it is in a normal state, and a switch circuit 62 which outputs the positive terminal voltage of the sensor element 20 to the ECU 50 through a signal line SL2 when it is in a normal state. Each of the switch circuits 61 and 62 is configured to be switchable from the normal state (the state shown in the figure) to a disconnection state (an open state), a battery short-circuit state, and a ground short-circuit state. Between the signal lines SL1 and SL2, a switch circuit 63 is connected. The switch circuit 63 is configured to be switchable from a normal state (the state shown in the figure) to a SL1-SL2 short-circuit state. The degradation simulator 30 further includes a switch circuit 64 through which a heater control line SL3 leads to the heater 28 from the ECU 50. The switch circuit 64 is configured to be switchable from a normal state (the state shown in the figure) to a disconnection state (an open state), a battery short-circuit state, and a ground short-circuit state. The above described switch circuits 61 to 64 are switched in accordance with switch signals from the microcomputer 32, or a not shown input operation section.

Each of the switch circuits 61, 62 and 64 is switchable to a selected one of the disconnection state, battery short-circuit state, and ground short-circuit state. Accordingly, two of these states, for example, the battery short-circuit state and ground short-circuit state are not set at the same time.

The degradation simulator 30 shown in FIG. 6 enables simulating a selected one of the following abnormalities by appropriately controlling the sates of the switch circuits 61 to 64.

(1) By setting the switch circuit 61 to the open state other than the normal state, battery short-circuit state, and ground short-circuit state, it is possible to simulate a disconnection abnormality at the negative terminal of the sensor.

(2) By setting the switch circuit 61 to the battery short-circuit state, it is possible to simulate a battery short-circuit abnormality at the negative terminal of the sensor.

(3) By setting the switch circuit 61 to the ground short-circuit state, it is possible to simulate a ground short-circuit abnormality at the negative terminal of the sensor.

(4) By setting the switch circuit 62 to the open state other than the normal state, battery short-circuit state, and ground short-circuit state, it is possible to simulate a disconnection abnormality at the positive terminal of the sensor.

(5) By setting the switch circuit 62 to the battery short-circuit state, it is possible to simulate a battery short-circuit abnormality at the positive terminal of the sensor.

(6) By setting the switch circuit 62 to the ground short-circuit state, it is possible to simulate a ground short-circuit abnormality at the positive terminal of the sensor.

(7) By setting the switch circuit 63 to the SL1-SL2 short-circuit state, it is possible to simulate a short-circuit abnormality between the negative and positive terminals of the sensor.

(8) By setting the switch circuit 64 to the open state other than the normal state, battery short-circuit state, and ground short-circuit state, it is possible to simulate a disconnection abnormality in the heater 28.

(9) By setting the switch circuit 64 to the battery short-circuit state, it is possible to simulate a battery short-circuit abnormality in the heater 28.

(10) By setting the switch circuit 64 to the ground short-circuit state, it is possible to simulate a ground short-circuit abnormality in the heater 28.

As explained above, according to the second embodiment, in addition to the degradation simulation concerning response delay (dead time delay, and time constant delay), abnormalities concerning the sensor element 20 and the heater 28 can be simulated.

Other Embodiments

It is a matter of course that various modifications can be made to above embodiments as described below.

The above embodiments are directed to a degradation simulator used for an A/F sensor capable of linearly detecting an air-fuel ratio (oxygen concentration) of an exhaust gas. However, the above embodiments are applicable to an $O_2$ sensor which outputs an electromotive force signal having a value depending on the air-fuel ratio of the exhaust gas. Like the A/F sensor, the $O_2$ sensor includes a solid electrolyte layer, and a pair of electrodes (an exhaust gas side electrode and a reference gas side electrode) located opposite to each other across from the solid electrolyte layer. The $O_2$ sensor outputs a substantially binary signal representing the air-fuel ratio being rich or lean with respect to a theoretical air-fuel ratio.

Figure 7:
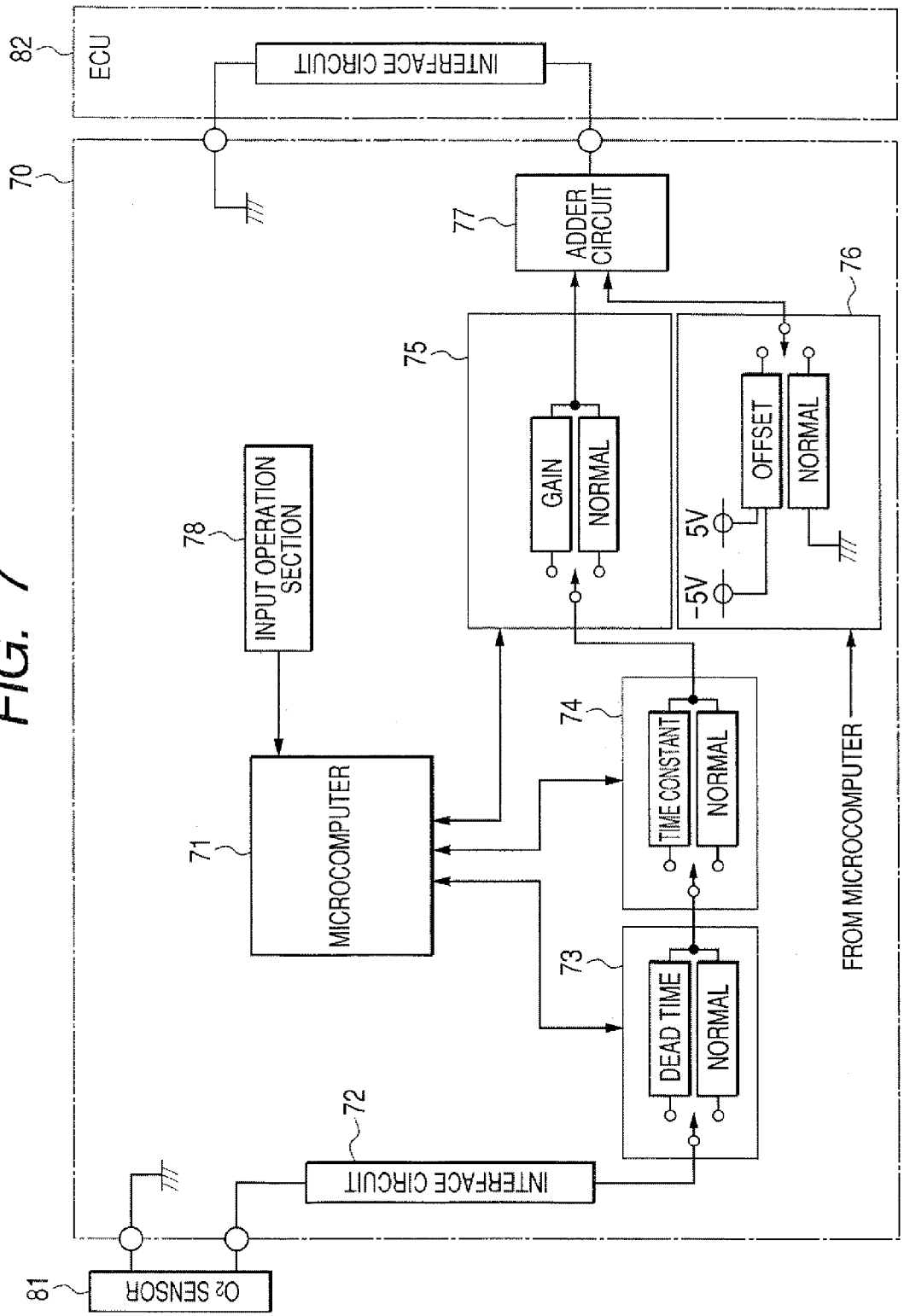
FIG. 7 is a diagram showing a structure of a degradation simulator for an O2 sensor according to a third embodiment of the invention.

FIG. 7 is a diagram of a degradation simulator 70 as a third embodiment of the invention, which is used for such an O₂ sensor.

As shown in this figure, the degradation simulator 70 is connected with an O₂ sensor 80 and an ECU 82. The degradation simulator 70 includes a microcomputer 71, an interface circuit 72, a dead time setting circuit 73, a time constant setting circuit 74, a gain setting circuit 75, an offset setting circuit 76, and an adder circuit 77. The dead time setting circuit 73, time constant setting circuit 74, and gain setting circuit 75 are connected in series. An output of the gain setting circuit 75 and an output of the offset setting circuit 76 are inputted to the adder circuit 77. Since the structures of the circuits 73 to 76 are respectively the same as those of the circuits 35 to 38 explained with reference to FIG. 1, the explanations thereof are omitted.

The degradation simulator 70 further includes an input operation section 78. Like the foregoing input operation section 41, the input operation section 78 enables a user to perform input operations including setting of the pseudo-degradation mode, switching between the symmetrical/asymmetrical modes, and volume adjustment. However, the degradation simulator 70 is configured to enable switching between the symmetrical/asymmetrical modes for a lean gas case and a rich gas case individually in generating a gain pseudo-degradation state. Accordingly, the input operation section 78 is provided with a symmetrical/asymmetrical changeover switch (not shown) for gain pseudo-degradation. That is, in this embodiment, the gain can be variably set individually for the lean gas case and the rich gas case.

Another difference between the degradation simulator 30 and the degradation simulator 70 is in that a degradation simulation is performed after the sensor output (element current signal) is subjected to current-voltage conversion in the degradation simulator 30 for the A/F sensor, while on the other hand, a degradation simulation is performed without the sensor output (the electromotive force signal) being subjected to current-voltage conversion in the degradation simulator 70 for the O₂ sensor.

Figure 8A:
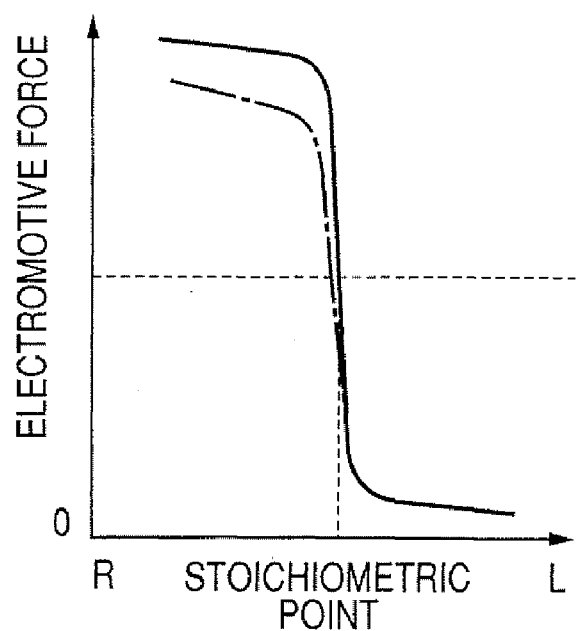
FIG. 8A and FIG. 8B are a graph showing an output characteristic of the O2 sensor respectively when gain degradation is present in a rich side and a lean side.
Figure 8B:
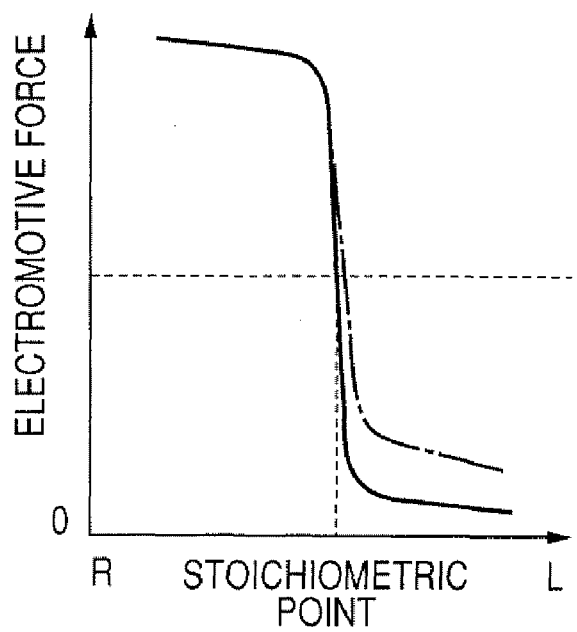

In the O2 sensor, gain degradation may occur differently for the rich side and the lean side. The solid line in each of FIG. 8A and FIG. 8B represents an electromotive force output characteristic of the O2 sensor. As shown in these figures, the electromotive force output characteristic of the O₂ sensor is originally symmetrical with respect to the stoichiometric point (the point where λ=1) between the rich side and the lean side. If gain degradation occurs in the rich side, the electromotive force output of the O₂ sensor is lowered in the rich side as shown by the chain line in FIG. 8A. On the other hand, if gain degradation occurs in the lean side, the electromotive force output of the O₂ sensor is lowered in the lean side as shown by the chain line in FIG. 8B. This embodiment enables simulating gain degradation even if it occurs differently for the rich side and the lean side, because of the provision of the symmetrical/asymmetrical changeover switch for gain pseudo-degradation.

The degradation simulator 70 may be configured to enable switching between the symmetrical/asymmetrical modes individually for the lean gas case and rich gas case also when simulating offset degradation, so that the offset can be variably set individually for the lean gas case and the rich gas case.

The degradation simulator 30 shown in FIG. 1 has the structure in which the dead time, the time constant, and the offset can be individually set as parameters in generating a pseudo-degradation state. However, the degradation simulator 30 may be so configured that at least the dead time and the time constant can be individually set as parameters in generating a pseudo-degradation state.

The degradation simulator 30 shown in FIG. 1 may be so configured that at least one of a maximum value (an upper limit value) of the dead time settable in the dead time setting circuit 35, and a maximum value (an upper limit value) of the time constant settable in the time constant setting circuit 36 is changeable. This is made possible, for example, by providing the degradation simulator 30 with a maximum value changeover switch which enables switching the maximum value between Tmax1 (1 second, for example) and Tmax2 (5 seconds, for example). This makes it possible to arbitrarily change an execution condition of the degradation simulation in accordance with a specification or product needs (an automobile manufacturer's requirement, for example) for a system including an A/F sensor to which the present invention is applied.

In the case where a maximum value of the dead time or the time constant is changeable, the setting range of the degradation simulation (the setting range of the dead time or the time constant) can be made wider by increasing the maximum value. On the other hand, if the maximum value is reduced, for example, by increasing an adjustment value per rotation angle (rotation adjustment resolution) when a rotary dial is used as the adjustment dial, it becomes easy to finely set the adjustment volumes.

The above embodiments in which the A/F sensor 10 is mounted on the exhaust pipe of the engine may be so configured that the adjustment value of the dead time or the time constant inputted through the input operation section 41 is corrected at every moment of time in accordance with the flow rate or flow speed of the exhaust gas flowing through the exhaust pipe. In more detail, they may be so configured as to measure the flow rate or flow speed of the exhaust gas during execution of the degradation simulation, the measurement being inputted to the microcomputer 32 to correct the adjustment value of the dead time or the constant time in accordance with the measurement. The flow rate or flow speed of the exhaust gas may be calculated on the basis of an intake air quantity.

The purpose of the above correction is to prevent lowering of accuracy of the degradation simulation. If the flow rate or flow speed of the exhaust gas changes, the response characteristic of the A/F sensor also changes. The change in the response characteristic of the A/F sensor may cause the accuracy of the degradation simulation to decrease. By correcting the adjustment value of the dead time or the time constant inputted through the input operation section 41 in accordance with the flow rate or flow speed of the exhaust gas, it becomes possible to prevent the accuracy of the degradation simulation from decreasing.

The degradation simulator 30 shown in FIG. 1 has the structure in which the setting signal of the pseudo-degradation mode, symmetrical/asymmetrical switching signal, and volume adjustment signal are inputted to the microcomputer 32. However, the degradation simulator 30 may be so configured that the setting signal of the pseudo-degradation mode, symmetrical/asymmetrical switching signal, and volume adjustment signal are directly inputted to the dead time setting circuit 35, time constant setting circuit 36, gain setting circuit 37, and offset setting circuit 38, respectively.

The degradation simulator 30 shown in FIG. 1 has the structure in which the setting of the pseudo-degradation mode, symmetrical/asymmetrical switching, and volume adjustment are performed by a user through the input operation section 41. However, the degradation simulator 30 may be so configured that the degradation simulations are executed by a predetermined simulation program. For example, a plurality of degradation patterns are simulated in succession by causing the microcomputer 32 to execute a degradation simulation process. In this case, the plurality of the degradation patterns are executed in succession while changing a combination pattern or a combination of setting values of the dead time degradation, constant time degradation, gain degradation, and offset degradation.

The second embodiment has been described with respect to the pseudo-disconnection state, pseudo-battery short-circuit state, and pseudo-ground short-circuit state as examples of pseudo-abnormal states of the sensor element 20 and the heater 28. However, the second embodiment may be so configured as to execute abnormality simulation for only one of the sensor element 20 and the heater 28. Also, the second embodiment may be so configured as to execute simulation with respect to only one or two of the pseudo-disconnection state, pseudo-battery short-circuit state, and pseudo-ground short-circuit state.

In the above embodiments, although the sensor element (A/F sensor) has bee described as a single-cell type sensor element having the structure shown in FIG. 3, it may have a different structure. For example, the sensor element may be a dual-cell type sensor element having a pump cell and an electromotive force cell. In other words, the structure of the sensor element is not limited to the one having a single solid electrolyte layer, but it may be the one having two or three solid electrolyte layers. The sensor element may be of the type having a cup-shape structure.

Next, an example of a dual-cell type sensor element and an example of a triple-cell type sensor element are explained with reference to FIG. 9A and FIG. 9B, respectively.

Figure 9A:
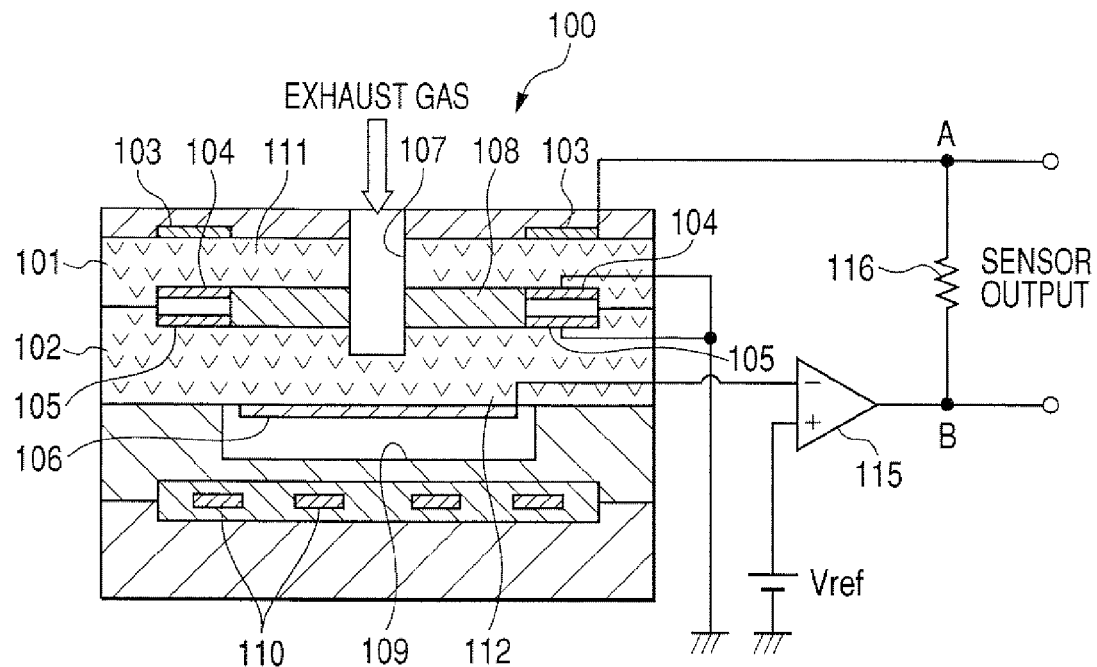
FIG. 9A is a cross-sectional view of a dual-cell type sensor element including two solid electrolyte layers, which can be a simulation object of the degradation simulator of the present invention.

The sensor element 100 shown in FIG. 9A includes two solid electrolyte layers 101 and 102. The solid electrolyte layer 101 is provided with a pair of electrodes 103 and 104 located opposite to each other. The solid electrolyte layer 102 is provided with a pair of electrodes 105 and 106 located opposite to each other. In FIG. 9A, although each of the electrodes 103 to 105 is shown as being separated into two parts, actually, these parts are connected to form a single electrode. In the sensor element 100, the solid electrolyte layer 101, and electrodes 103, 104 constitute a pump cell 111, while the solid electrolyte layer 102, and electrodes 105, 106 constitute an oxygen detection cell 112. The sensor element 100 has a laminated structure as in the case of the foregoing sensor element 20. In FIG. 9A, the reference numeral 107 denotes a gas introduction hole, 108 denotes a porous diffusion layer, 109 denotes an atmospheric duct, and 110 denotes a heater.

The voltage of the electrode 106 of the oxygen detection cell 112 is applied to a negative input terminal of a comparator 115, while a reference voltage Vref is applied to a positive input terminal of the comparator 115. Between the electrode 103 of the pump cell 111 and an output terminal of the comparator 115, a current measuring resistor 116 is connected. The voltage across both ends A and B of the current measuring resistor 116 is taken out as a sensor output.

The oxygen detection cell 112 of the sensor element 100 having the above described structure generates a binary electromotive force output (low voltage of 0 V or high voltage of 0.9 V) depending on whether an exhaust gas under measurement is lean or rich with respect to the stoichiometric point. When the exhaust gas is lean, since the electromotive force output of the oxygen detection cell 112 is low, the output of the comparator 115 (the voltage at the point B in FIG. 9A) is at a high level. As a result, a current flows through the current measuring resistor 116 in the direction from B to A. On the other hand, when the exhaust gas is rich, since the electromotive force output of the oxygen detection cell 112 is high, the output of the comparator 115 (the voltage at the point B in FIG. 9A) is at a low level. As a result, a current flows through the current measuring resistor 116 in the direction from A to B. Incidentally, the oxygen detection cell 112 is also referred to as "electromotive force cell" or "oxygen concentration detection cell".

Figure 9B:
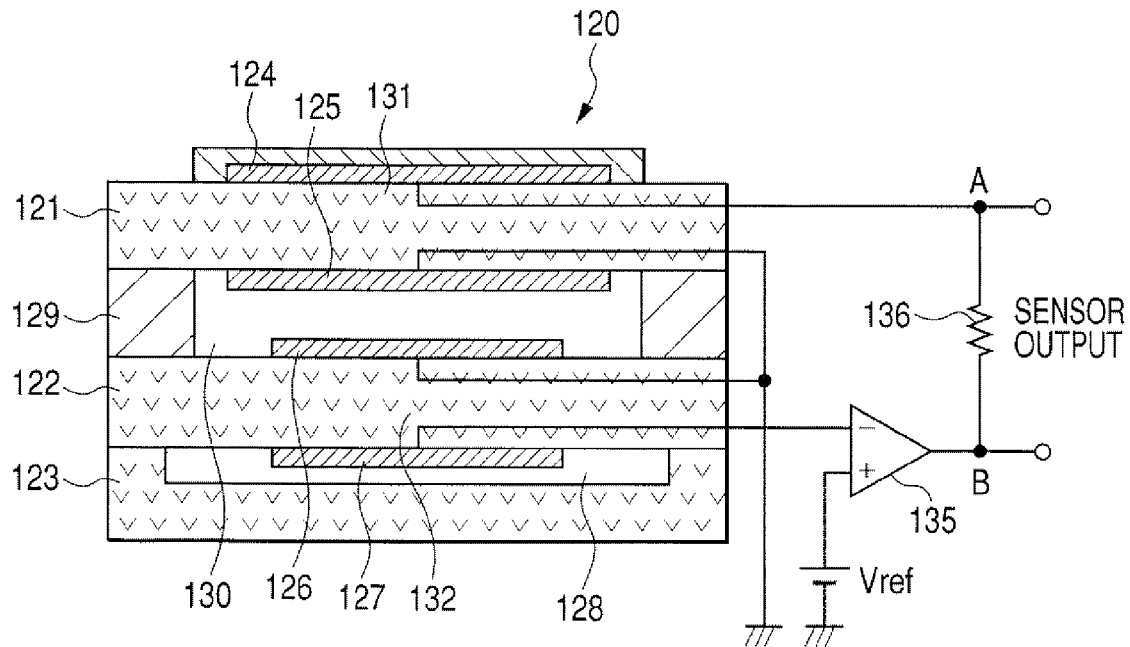
FIG. 9B is a cross-sectional view of a triple-cell type sensor element including three solid electrolyte layers, which can be a simulation object of the degradation simulator of the present invention.

The sensor element 120 shown in FIG. 9B includes three solid electrolyte layers 121, 122 and 123. The solid electrolyte layer 121 is provided with a pair of electrodes 124 and 125 located opposite to each other. The solid electrolyte layer 122 is provided with a pair of electrodes 126 and 127 located opposite to each other. The solid electrolyte layer 121, and electrodes 124, 125 constitute a pump cell 131. The solid electrolyte layer 122, and electrodes 126, 127 constitute an oxygen detection cell 132. The solid electrolyte layer 123 serves as a wall member to form an oxygen reference chamber 128. The sensor element 120 has a laminated structure as in the case of the foregoing sensor element 20. In FIG. 9B, the reference numeral 129 denotes a porous diffusion layer, and 130 denotes a gas detection chamber. The oxygen detection chamber 132 is also referred to as "electromotive force cell" or "oxygen concentration detection cell".

The voltage of the electrode 127 of the oxygen detection cell 132 is applied to a negative input terminal of a comparator 135, while a reference voltage Vref is applied to a positive input terminal of the comparator 135. Between the electrode 124 of the pump cell 131 and an output terminal of the comparator 135, a current measuring resistor 136 is connected. The voltage across both ends A and B of the current measuring resistor 136 is taken out as a sensor output. A current flows through the current measuring resistor 136 in the direction from B to A when an exhaust gas under measurement is lean, while a current flows through the current measuring resistor 136 in the direction from A to B when the exhaust gas is rich.

Figure 10A:
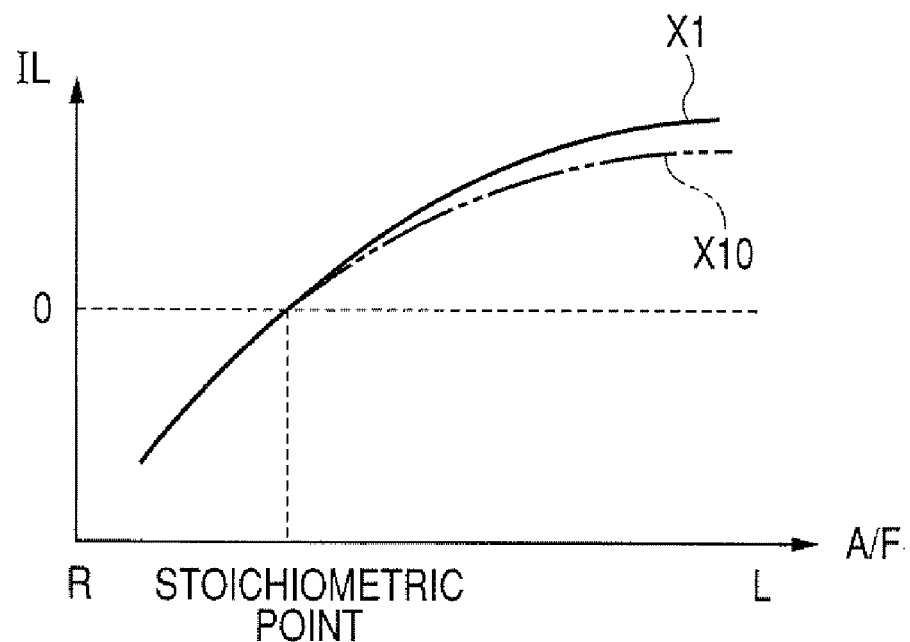
FIG. 10A and FIG. 10B are a graph showing an output characteristic of the dual-cell type or triple-cell type sensor element shown in FIG. 9A or FIG. 9B respectively when gain degradation is present in a lean side and a rich side.
Figure 10B:
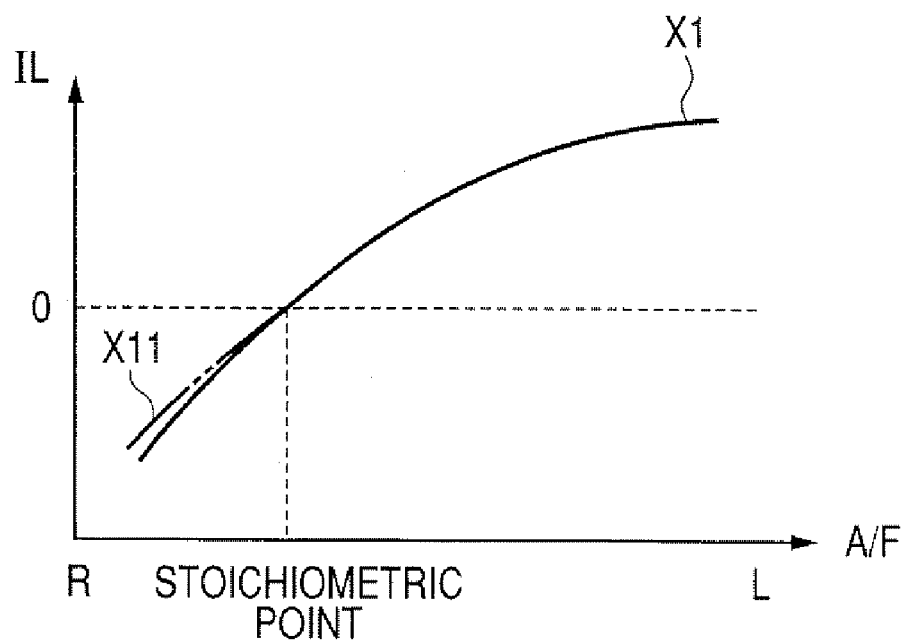

In the dual-cell type sensor element 100 and the triple-cell type sensor element 120 having the oxygen detection cell (the electromotive force cell) may undergo gain degradation at the rich side and the lean side individually as has been explained with reference to FIG. 8. Accordingly, the sensor output also may undergo gain degradation at the rich side and the lean side individually. Hence, it may occur that gain degradation occurs only at the lean side as shown in FIG. 10A, or only at the rich side as shown in FIG. 10B. In FIGS. 10A and 10B, the solid line X1 represents a basic sensor output characteristic when no gain degradation is present, and each of the double-dashed lines X10 and X1 represents a sensor output characteristic when gain degradation is present.

By provision of symmetrical/asymmetrical switching means for generating pseudo-gain degradation, gain degradation different for the rich side and the lean side can be properly simulated. A symmetrical/asymmetrical switching means may be provided also for generating pseudo-offset degradation.

The present invention is applicable to a gas sensor other than an A/F sensor and an $O_2$ sensor which measure concentration of O2. For example, the present invention is applicable to a hybrid type gas sensor including two cells formed by solid electrolyte layers, a first cell (a pump cell) of which operates to remove oxygen from a gas under measurement, a second cell (a sensor cell) of which operates to measure concentration of a specific gas component in the gas from which oxygen has been removed.

Such a hybrid type gas sensor is used as, for example, a NOx sensor for measuring NOx concentration of an exhaust gas. The hybrid type gas sensor may further include a third cell (a monitor cell, or a second pump cell) operating to measure remaining oxygen concentration of the exhaust gas from which oxygen has been removed.

The present invention is also applicable to a gas sensor for measuring HC concentration or CO concentration. This gas sensor is configured to decompose HC or CO from a gas under measurement from which oxygen has been removed by the pump cell, in order to measure HC concentration or CO concentration.

The present invention is also applicable to a gas sensor located in an engine intake pipe, a gas sensor used for control of an engine other than a gasoline engine, such as a diesel engine, and a gas sensor used for other than vehicles.

The above explained preferred embodiments are exemplary of the invention of the present application which is described solely by the claims appended below. It should be understood that modifications of the preferred embodiments may be made as would occur to one of skill in the art.

What is claimed is:

1. A degradation simulator for a gas sensor including a sensor element having a solid electrolyte layer and a pair of electrodes located opposite to each other across from said solid electrolyte layer, and an element cover surrounding said sensor element and formed with a vent hole to introduce an ambient gas into said sensor element, said sensor element outputting a sensor output signal having a value depending on concentration of a specific gas in said ambient gas, said degradation simulator comprising:
a first setting function of enabling variably setting a time constant delay which appears on said sensor output signal when concentration of said specific gas changes;
a second setting function of enabling variably setting a dead time delay which appears on said sensor output signal when concentration of said specific gas changes; and
an adding function of adding at least one of said time constant delay set by said first function and said dead time delay set by said second function to said sensor output signal in order to generate a pseudo-degraded sensor output signal in accordance with an external instruction.

2. The degradation simulator according to claim 1, in which said first setting function is configured to enable setting said time constant delay individually for a first case where concentration of said specific gas increases, and a second case where concentration of said specific gas decreases, and said second setting function is configured to enable setting said dead time delay individually for said first and second cases.

3. The degradation simulator according to claim 1, further comprising a switching function of enabling selecting between a symmetrical mode where each of said time constant delay and said dead time delay is symmetrical in value between a first case where concentration of said specific gas increases and a second case where concentration of said specific gas decreases, and an asymmetrical mode where each of said time constant delay and said dead time delay is asymmetrical in value between said first and second cases.

4. The degradation simulator according to claim 1, further comprising a third setting function of enabling variably setting a gain of said sensor output signal, and a fourth setting function of enabling variably setting an offset of said sensor output signal, said adding function is configured to add at least one of said time constant delay set by said first function, said dead time delay set by said second function, said gain set by said third setting function, and said offset set by said fourth setting function to said sensor output signal in order to generate a pseudo-degraded sensor output signal.

5. The degradation simulator according to claim 1, further comprising a third setting function of enabling variably setting a gain of said sensor output signal, and a fourth setting function of enabling variably setting an offset of said sensor output signal, said adding function is configured to add at least one of said time constant delay set by said first function and said dead time delay set by said second setting function, and at least one of said gain set by said third setting function and said offset set by said fourth setting function to said output signal in order to generate a pseudo-degraded sensor output signal.

6. The degradation simulator according to claim 4, wherein said sensor element includes an electromotive force cell outputting an electromotive force signal having a value depending on concentration of said specific gas as said sensor output signal, said first and second setting functions are so configured that one of said gain and said offset is set individually for a first case where concentration of said ambient gas is a rich gas and a second case where said ambient gas is a lean gas.

7. The degradation simulator according to claim 5, wherein said sensor element includes an electromotive force cell outputting an electromotive force signal having a value depending on concentration of said specific gas as said sensor output signal, said first and second setting functions are so configured that one of said gain and said offset is set individually for a first case where concentration of said ambient gas is a rich gas and a second case where said ambient gas is a lean gas.

8. The degradation simulator according to claim 1, wherein said first and second setting functions are so configured that at least one of a maximum value of said constant time delay and a maximum value of said dead time delay is adjustable.

9. The degradation simulator according to claim 1, further comprising an abnormality simulating function of enabling generation of a pseudo-sensor output signal simulating one of disconnection or short-circuit of signal lines leading to said sensor element.

10. The degradation simulator according to claim 9, further comprising a switch function of enabling setting said signal lines in one of an open state, a power supply short-circuit state, a ground short-circuit state, and a line-to-line short-circuit state.

11. The degradation simulator according to claim 1, wherein said sensor element includes therein a heater, and said degradation simulator further comprises an abnormality simulating function of enabling generation of a pseudo-signal simulating disconnection or short-circuit of a power supply line leading to said heater.

12. The degradation simulator according to claim 11, further comprising a switch function of enabling setting said power supply line in one of an open state, a power supply short-circuit state, and a ground short-circuit state.

13. The degradation simulator according to claim 1, wherein said gas sensor is mounted on an exhaust gas pipe of an internal combustion engine, said ambient gas being an exhaust gas, and said degradation simulator further comprises a function of correcting at least one of said time constant delay set by said first function and said dead time delay set by said second function in accordance with a flow rate or a flow speed of said exhaust gas.

14. The degradation simulator according to claim 1, wherein said gas sensor is mounted on an intake air pipe of an internal combustion engine, said ambient gas being an intake air, and said degradation simulator further comprises a function of correcting at least one of said time constant delay set by said first function and said dead time delay set by said second function in accordance with a flow rate or a flow speed of said intake.

* * * * *